United States Patent [19]

Ward

[11] Patent Number: 4,568,375

[45] Date of Patent: Feb. 4, 1986

[54] 2-SUBSTITUTED 5-AMINO-3-OXO-4-(SUBSTITUTED-PHENYL)-2,3-DIHYDROFURAN HERBICIDES

[75] Inventor: Carl E. Ward, San Jose, Calif.

[73] Assignee: Chevron Research Company, San Francisco, Calif.

[21] Appl. No.: 666,075

[22] Filed: Oct. 26, 1984

[51] Int. Cl.$^4$ .................. A01N 43/08; C07D 307/52
[52] U.S. Cl. .......................... 71/88; 71/94; 71/95; 260/239 A; 546/214; 546/283; 548/517; 549/477; 549/479; 204/157.69
[58] Field of Search .............. 549/477, 479; 260/239 A; 546/214, 283; 548/517; 71/88, 94, 95; 204/158 HA

[56] References Cited

U.S. PATENT DOCUMENTS 4,441,910  4/1984  Shapiro .................................. 71/90

FOREIGN PATENT DOCUMENTS 42-19090  9/1967  Japan .
44-13710  6/1969  Japan .
1521092   8/1978  United Kingdom .
2080289   2/1982  United Kingdom .

OTHER PUBLICATIONS

Capraro et al., Helvetica Chimica Acta., vol. 66, No. 31, (1983), pp. 362–378.
Umio et al., Chemical Abstracts, vol. 70, (1969), 68123t.
Volovenko et al., Chemical Abstracts, vol. 95, (1981), 24799e.
Meier et al., Chemical Abstracts, vol. 94, (1981), 138818v.

Primary Examiner—Richard L. Raymond
Attorney, Agent, or Firm—T. G. DeJonghe; L. S. Squires

[57] ABSTRACT

2-Halo and 2-alkoxy-5-amino-3-oxo-4-(substituted-phenyl)-2,3-dihydrofuran and derivatives thereof. The 2-alkoxy and 2-fluoro compounds generally exhibit both pre-emergence and post-emergence phytotoxicity and are useful as herbicides and also at low dosages as plant growth regulating agents. The 2-bromo, chloro and iodo compounds are primarily useful as intermediates for the 2-alkoxy and 2-fluoro analogs.

40 Claims, No Drawings

2-SUBSTITUTED 5-AMINO-3-OXO-4-(SUBSTITUTED-PHENYL)-2,3-DIHYDROFURAN HERBICIDES

BACKGROUND OF THE INVENTION

This invention relates to 2-halo, and 2-alkoxy-5-amino-3-oxo-4-(substituted-phenyl)-2,3-dihydrofuran derivatives and to the use of such compounds as intermediates and herbicides and plant growth regulators.

Chemiker-Zeitung 104 (1980) No. 10, Pages 302–303, is an academic paper disclosing the ring closure of 1-(dimethylamino)-2,4-diphenyl-1-buten-3,4-dione to yield 5-dimethylamino-2,4-diphenyl-2,3-dihydrofuran. British Pat. No. 1,521,092, discloses certain 3-phenyl-5-substituted-4(1H)-pyrid-ones or -thiones as herbicides. Japanese Patent Application 13,710/69 (Chemical Abstracts 71:61195e) discloses the generic formula for 5-amino-3-oxo-4-(phenyl and halophenyl)-2,3-dihydrofuran and specifically discloses 5-amino-3-oxo-4-(phenyl and 4-chlorophenyl)-2,3-dihydrofurans. Japanese Pat. No. 19090 (Chemical Abstracts 69P10352e) discloses certain 2,3-dihydrothiophenes as pharmaceuticals. *Helvetica Chemica Acta*, Volume 66, Pages 362–378 (1983) discloses 5-N-cyclopropyl-4-phenyl-2-methoxycarbonylmethylene-3-furanone as part of an academic chemical synthesis discussion. U.S. Pat. No. 4,441,910 discloses herbicidal ureidosulfonylfurans and ureidosulfonylthiophenes.

In my copending application Ser. No. 607,610, filed May 9, 1984, and now abandoned I disclose a number of 2-substituted-3-oxo-4-(substituted phenyl)-2,3-dihydrofuran derivatives and the utility of said derivatives as herbicides and plant growth regulators.

SUMMARY OF THE INVENTION

The present invention provides compounds having pre-emergence and post-emergence herbicidal activity and also compounds which although only having modest herbicidal activity, are useful as intermediates for preparing products having especially good pre-emergence activity against a broad spectrum of both broadleaf weeds and grassy weeds. The compounds also exhibit plant growth regulating properties.

The compounds of the present invention can be represented by the following formula:

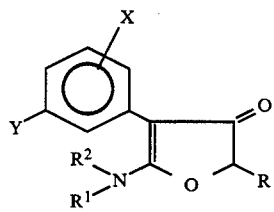

(I)

wherein R is fluoro, chloro, bromo, iodo or lower alkoxy; or alkenylmethoxy having 3 through 8 carbon atoms, preferably 3 through 6 carbon atoms;

$R^1$ is alkyl having 1 through 4 carbon atoms;

$R^2$ is alkyl having 1 through 4 carbon atoms; alkenyl having 3 or 4 carbon atoms; lower alkoxycarbonylalkyl having from 1 through 4 carbon atoms in the alkoxy moiety and from 1 through 4 carbon atoms in the alkyl moiety; lower alkoxyalkyl wherein the alkoxy and alkyl moieties independently having 1 through 3 carbon atoms; or lower alkylthioalkyl wherein the alkyl moieties independently having 1 through 3 carbon atoms; or $R^1$ and $R^2$ together with the nitrogen to which they are joined form a saturated nitrogen heterocycle having from 4- through 6-ring atoms one of which is the joining nitrogen atom and the remainder of which are carbon atoms or an unsaturated heterocycle selected from the group of 2-pyrrolin-1-yl; 3-pyrrolin-1-yl; 1,2,3,4-tetrahydropyrid-1-yl and 1,2,5,6-tetrahydropyrid-1-yl;

X is hydrogen, lower alkyl, lower alkoxy, halo, or trifluoromethyl and can be at any available position on the phenyl ring; and Y is lower alkyl, lower alkoxy; halo; lower haloalkyl having 1 through 4 carbon atoms and 1 to 3 of the same or different halo atoms; lower haloalkoxy having 1 through 4 carbon atoms and 1 through 3 of the same or different halo atoms; or lower haloalkylthio having 1 through 4 carbon atoms and 1 through 3 of the same or different halo atoms.

The invention also comprises compatible salts of the compound of Formula (I), for example salts obtained via replacement of the amino hydrogen (i.e., $R^1$ and $R^2$ is hydrogen) with a compatible cation or enolation of the 3-oxo group following replacement of the amino hydrogen.

The compounds of Formula (I) exist as keto⇌enol isomers. The compounds also have an asymmetric carbon atom and can also exist as optical isomers. In some instances the compounds also exist as geometric isomers. The above formula is intended to encompass the respective individual isomers as well as mixtures thereof and the respective isomers as well as mixtures thereof are encompassed within the invention.

The presence of a 3-trifluoromethyl substituent on the 4-phenyl group of the compounds of the present invention generally very substantially enhances herbicidal activity especially in the products prepared from the present compounds.

In a further aspect the invention provides a herbicidal composition comprising a compatible carrier and a herbicidally effective amount of the compounds of Formula (I), or compatible salts thereof, or mixtures thereof.

The present invention also provides a method for preventing or controlling the growth of unwanted vegetation, which comprises treating the growth medium and/or the foliage of such vegetation with a herbicidally effective amount of the compound(s) of Formula (I) and/or compatible salts thereof.

In another aspect, the present invention provides a plant growth regulating composition comprising a compatible carrier and a plant growth regulating amount of the compound of Formula (I), compatible salts of Formula (I), or mixtures thereof, effective to alter the normal growth pattern of said plants.

The present invention also provides a method for regulating plant growth which comprises treating the growth medium and/or the foliage of such vegetation with a plant growth regulating effective amount of the compound(s) of Formula (I) and/or compatible salts thereof, effective to alter the normal growth pattern of said plants.

The present invention also provides chemical intermediates and processes for preparing the compounds of Formula (I).

The invention will be further described hereinbelow.

FURTHER DESCRIPTION OF THE INVENTION AND THE PREFERRED EMBODIMENTS

Illustrations of typical compounds of Formula (I) of the present invention can be had by reference to Examples 2, 3, 6–10 set forth hereinbelow on Pages 24–30 and 33–51. In terms of substituents, the preferred compounds are those wherein $R^1$ and $R^2$ are independently methyl, ethyl or n-propyl, and more preferably $R^1$ and $R^2$ are independently methyl or ethyl; X is hydrogen and/or Y is 3-trifluoromethyl or 3-halo, especially 3-trifluoromethyl. Most preferably the compounds contain a combination of two or more preferred substituents. In terms of the use of the compounds as herbicides per se, the preferred R substituent is fluoro, lower alkoxy or alkenylmethoxy or more preferably, lower alkoxy, especially ethoxy, propoxy, isopropoxy and t-butoxy. In terms of the use of the compounds as intermediates, the preferred R substituents are chloro, bromo, and iodo, and especially bromo.

The compounds of the present invention wherein R is chloro, bromo, or iodo can be prepared via the following schematically represented process:

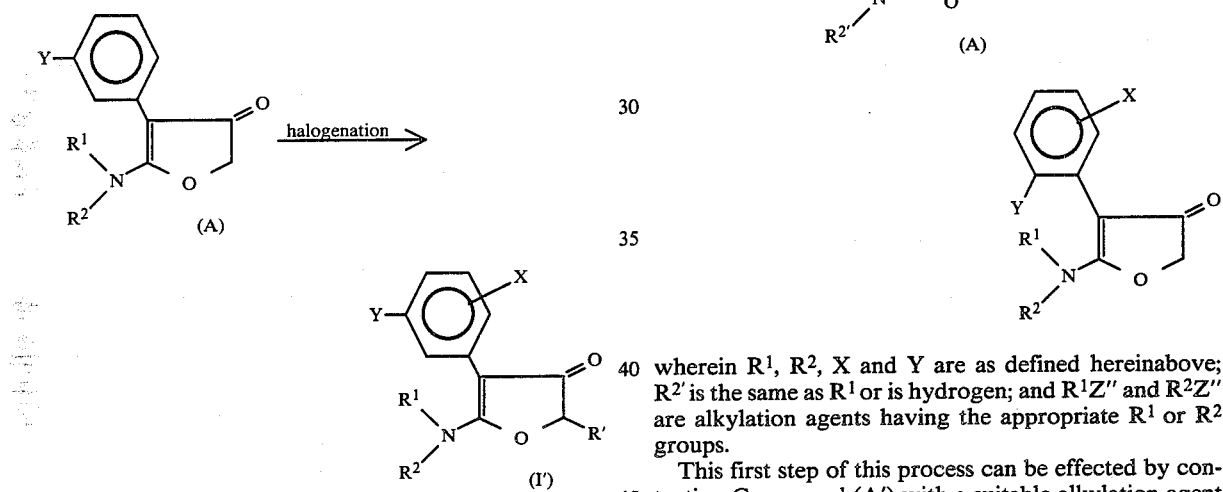

wherein R' is chloro, bromo, or iodo and $R^1$, $R^2$, X and Y are as defined hereinabove.

This process can be conveniently effected by contacting compound A with the appropriate N-chloro, N-bromo or N-iodosuccinimide under ultra-violet irradiation, preferably in the presence of a suitable catalyst and preferably in an inert organic solvent.

Typically, this process is conducted by irradiating the reaction mixture with light having a wave length of about 320 nm to 600 nm for about 1 to 5 hours. Temperature is generally not critical and typically temperatures in the range of 0° to 100° C. Typically, about 1 to 2 moles, preferably about 1 to 1.1 moles of N-halosuccinimide and about 0 to 1, about 1 to 2 moles, preferably 1 to 1.1 moles, of N-bromosuccinimide and about 0 to 1, preferably 0.05 to 0.1 mole of catalyst are used per mole of compound A.

Suitable catalysts which can be used include, for example, dibenzoyl, peroxide, di-t-butylperoxide, azobisisobutyronitrile, and the like. Suitable inert organic solvents which can be used include, for example, carbon tetrachloride, chlorobenzene, 1,2-dichloroethane, tetrachloroethylene, methylene chloride, and the like and compatible mixtures thereof.

The N-halosuccinimides are known compounds and can be prepared via known procedures.

The intermediates of Formula A can be prepared by alkylation of the amino group of the corresponding 5-unsubstituted amino derivatives (Formula A')

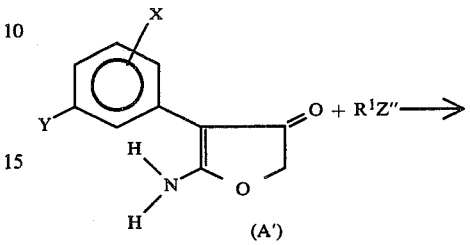

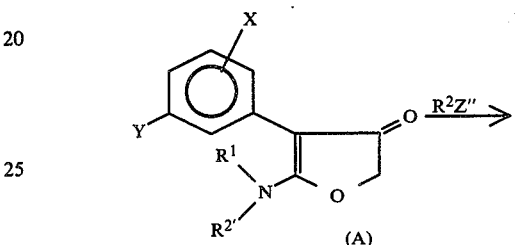

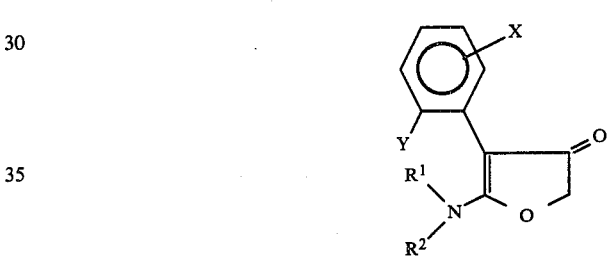

wherein $R^1$, $R^2$, X and Y are as defined hereinabove; $R^{2'}$ is the same as $R^1$ or is hydrogen; and $R^1Z''$ and $R^2Z''$ are alkylation agents having the appropriate $R^1$ or $R^2$ groups.

This first step of this process can be effected by contacting Compound (A') with a suitable alkylation agent capable of alkylating primary or secondary amino groups.

For example, this can be effected by contacting Compound (A') with $R^1$ iodide or bromide, preferably in an inert organic solvent and preferably in the presence of a scavenger base. Typically, this process is conducted at temperatures in the range of about from 0° to 100° C., preferably 20° to 45° C. for about from 1.0 to 72.0, preferably 2.0 to 18.0 hours. Where it is desired to monoalkylate, then typically about from 1.0 to 1.1 moles of $R^1$ halide reactant is used per mole of Compound (A'). Where it is desired to alkylate both amino hydrogens, then typically about from 1.9 to 4.0 moles of $R^1$ halide are used per mole of Compound (A'). In the case where it is desired to prepare the compound wherein $R^1$ is alkoxyalkyl or alkylthioalkyl, it is preferred to use a large excess of $R^1$ halide even where monoalkylation is desired; for example 3 to 6 moles of $R^1Z''$ per mole of D. If necessary, dialkylaton can be effected in a second step. Variation in $R^1$ and $R^2$ can be effected by first alkylating only one of the two amino hydrogens and then repeating the alkylation step with an alkylating agent having a different $R^2$ group. The compounds wherein $R^1$ and $R^2$ together with the amino nitrogen atoms form a saturated heterocycle can be prepared by using the appropriate $Z''\text{-}(CH_2)_{2\text{-}5}\text{-}Z''$, (wherein $Z''$ is Cl or Br) alkylating agent. The $R^1R^2N$ unsaturated heterocycle can be prepared by using the appropriate cis-alkenyl dihalide, wherein one of the halo atoms is on each of the terminal alkenyl carbon. Suitable inert organic solvents which can be used, include, for example, liquid halogenated alkanes; for example, methylene chloride, carbon tetrachloride, or dichloroethane; also useful are tetrahydrofuran and the like. Suitable scavenger bases which can be used include, for example, alkali metal alkanolates, for example, sodium methoxide, sodium ethoxide, potassium ethoxide, sodium hydride, potassium hydride, and the like.

The compounds of Formula (A) wherein $R^1$ and $R^2$ are each lower alkyl (e.g. methyl), are advantageously prepared using dialkyl sulfate as the alkylating agent. This can be conveniently effected by contacting the compound of Formula A' with the desired lower alkyl sulfate in the presence of a strong base and preferably in an inert organic solvent in the presence of a phase transfer agent. Typically, this process is conducted at temperatures in the range of about from 0° to 100° C., preferably 20° to 45° C., using about from 1.0 to 4.0 moles of dialkyl sulfate per mole of Compound I. An excess, typically about 2.5 mole of base is used. Preferably, this process is also conducted in an inert organic solvent such as, for example, methylene chloride, carbon tetrachloride, dichloroethane, tetrahydrofuran, and the like.

Suitable strong bases which can be used include, for example, sodium hydroxide, potassium hydroxide, sodium ethoxide, sodium carbonate, potassium carbonate, and the like. Suitable phase transfer agents are agents which transfer hydrophilic ions into a lipophilic organic medium and include, for example, benzyl triethylammonium chloride, tetra-n-butylammonium chloride, methyltrioctylammonium chloride, and the like.

The 5-unsubstituted amine precursors for the starting materials of formula A' can be prepared via cyclization of the corresponding substituted phenyl methoxyacetylacetonitrile

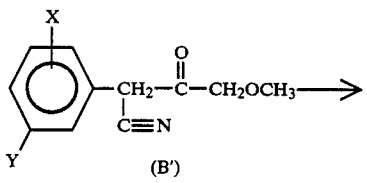

(B')

This process can be conveniently effected by contacting compound (B') with a cyclizing agent, under reactive conditions, preferably in an inert organic solvent.

Typically, this process is conducted at temperatures in the range of about from 0° to 200° C., preferably about from 115° to 120° C., for about 10 to 120 minutes, preferably about from 10 to 30 minutes, using about from 1 to 10, preferably 1 to 2, moles of cyclizing agent per mole of Compound (A'). Suitable cyclizing agents which can be used include, for example, strong anhydrous acids, for example, sulfuric acid, hydrogen chloride, hydrogen bromide, trifluoroacetic acid, methane sulfonic acid, and the like. Best results are typically obtained using anhydrous sulfuric acid. Suitable inert organic solvents which can be used include, for example, acetic acid, propionic acid, butyric acid, toluene, xylene, and the like, and compatible mixtures thereof.

The starting materials of Formula (B') can be prepared by the following schematically represented process:

[Structure: X-substituted phenyl-$CH_2CN$ + $R^{11}OCCH_2OR^{10}$ (with C=O) $\longrightarrow$ (B')]

(B)        (C')

wherein $R^{11}$ is lower alkyl (preferably methyl) and $R^{10}$, Y and X are as defined hereinabove.

This process can be conveniently effected by contacting Compound (B) with Compound (C'), and a strong base under reactive conditions, preferably in an inert organic solvent.

Typically, this process is conducted using the same conditions as described hereinabove with respect to the preparation of Compound (A') save that reaction C' is used in place of reactant C. The reactants of Formula C' are simple alkyl alkoxyacetate esters, for example, methyl methoxyacetate. The preparation of such compounds is well known to the art.

The starting materials of Formula (B) are generally known materials and can be prepared by known procedures, or obvious modifications thereof (i.e., substitution of appropriate starting materials). The preparation of Compound (B) is for example described in Org. Syn. Coll., Volume 1, 107 (1941).

The compounds of Formula (A') wherein $R^1$ and $R^2$ are each hydrogen can also be prepared via the general process schematically represented by the following overall reaction equation:

[Structure: X,Y-substituted phenyl-$CH_2CN$ + $H-C(OH)(H)-C(=O)-OR^5 \longrightarrow$]

(B)        (E)

[Structure: X,Y-substituted phenyl furanone with $H_2N$ group $=O + R^5OH$]

(A')

wherein R, and X and Y are as defined hereinabove; and $R^5$ is lower alkyl, aryl (e.g. phenyl) or arylalkylene (e.g. benzyl). Most typically, $R^5$ will be methyl.

This process can be conveniently effected by contacting Compound (B) with Compound (E), and a strong base (e.g. sodium methoxide, sodium ethoxide), preferably in an inert organic solvent.

Typically, this process is conducted at temperatures in the range of about from 0° to 100° C. preferably 75° to 85° C. for about from 5 to 36 hours, preferably 18 to 24 hours, using about from 1.0 to 10.0, preferably 1.0 to 1.2 moles of Compound (E) per mole of Compound (B). Also suitable inert organic solvents which can be used include, for example, lower alkanols (e.g. methanol, ethanol, propanol, etc.); tetrahydrofuran; dimethoxyethane; dioxane; and the like, and compatible mixtures thereof.

Suitable bases which can be used for this process include those bases previously described with respect to the reaction of Compound (B) with Compound (C).

The hydroxy esters of Formula (E) are also generally known compounds and can be prepared by known procedures or by obvious modifications thereof (e.g., by using appropriately substituted starting materials).

The compounds of Formula I wherein R is fluoro can be conveniently prepared via replacement of the 2-bromo, chloro, or iodo substituent from compound I' with a fluoro group:

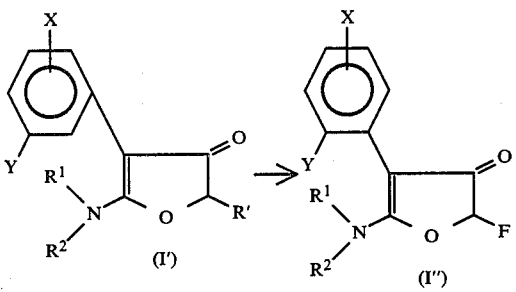

wherein R', $R^1$ and $R^2$ are as defined hereinabove.

This process can be conveniently effected by contacting compound I' with an alkali metal fluoride (e.g. sodium fluoride) preferably in an inert organic solvent.

Typically, this process is conducted at temperatures in the range of about from 25° to 90° C., preferably 80° to 85° C. for about from 12 to 36 hours, preferably 12 to 18 hours, using about from 1.0 to 5, preferably 1.5 to 2 moles of alkali metal fluoride per mole of compound (I'). Suitable inert organic solvents which can be used includes, for example, acetonitrile, dimethylformamide, dimethylsulfoxide, and the like.

The cmpounds of Formula A can also be conveniently prepared by applying the amination procedure described in the commonly assigned application of P. Pomidor, Ser. No. 666,078 filed on even date herewith, which procedure is hereby incorporated by reference.

As before noted, the compounds of Formula I wherein R is bromo, chloro or iodo are especially useful as intermediates for more active herbicides. Thus, these compounds can be expeditiously used to prepare the corresponding 2-alkoxy and 2-alkenylmethoxy analogs. This can be effected via the following schematically represented process.

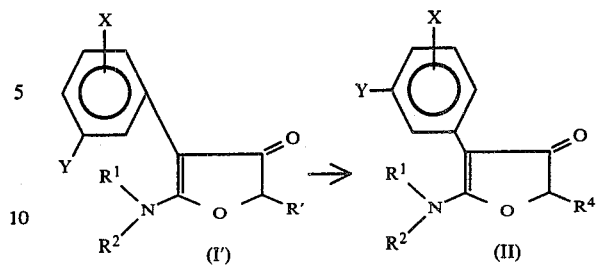

wherein $R^4$ is lower alkoxy or alkenylmethoxy having 3 through 8 carbon atoms, preferably 3 through 6 carbon atoms; and $R^1$, $R^2$ and R' are as defined hereinabove; preferably R' is bromo.

This process can be conveniently effected by contacting compound I' with an alkali metal alkanolate under reactive conditions, preferably in an inert organic solvent.

Typically, this process is conducted at temperatures in the range of about from 10° to 100° C., preferably 20° to 25° C. for about from 1 to 10 hours using about from 1 to 10, preferably 1 to 2 moles of alkanolate salt per mole of compound (I').

Suitable inert organic solvents which can be used include, for example, liquid alcohols, tetrahydrofuran, dimethoxyethane, dioxane, and the like. The alkali metal alkanolate can be conveniently prepared in situ by using the appropriate alkanol as the solvent. Correspondingly, where an alkanol is used as the solvent, it should correspond to the alkali metal alkanolate.

The compatible salts of Formula (I) can be prepared by conventional procedures for example by treating the compound of Formula (I) wherein $R^1$ and/or $R^2$ are hydrogen with a suitable strong base such as, for example, n-butyllithium, sodium hydride, potassium hydride, and the like, having the desired cation, by conventional procedures to yield the corresponding $R^1$ and/or $R^2$ cation salts. The enolate salts can be prepared by treating the $R^1$ and/or $R^2$ cation salts with base via conventional procedures. Additional variations in the salt cation can also be effected via ion exchange with an ion exchange resin having the desired cation.

General Process Conditions

In the above-described processes, it is generally preferable to separate the respective products before proceeding with the next step in the reaction sequence, except where described as an in situ step or unless otherwise expressly stated. These products can be recovered from their respective reaction product mixtures by any suitable separation and purification procedure, such as, for example, recrystallization and chromatography. Suitable separation and purification procedures are, for example, illustrated in the Examples set forth hereinbelow.

Generally, the reactions described above are conducted as liquid phase reaction and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, etc.) have been given, that other process conditions could also be used. Optimum reaction conditions (e.g., temperature, reaction time, mol ratios, solvents, etc.) may vary with the particular reagents or organic solvents used but can be determined by routine optimization procedures.

Where optical isomer mixtures are obtained, the respective optical isomers can be obtained by conventional resolution procedures. Geometric isomers can be separated by conventional separation procedures which depend upon differences in physical properties between the geometric isomers.

Definitions

As used herein the following terms have the following meanings unless expressly stated to the contrary:

The term "lower alkyl" refers to both straight- and branched-chain alkyl groups having a total of from 1 through 4 carbon atoms and includes a primary, secondary and tertiary alkyl groups. Typical lower alkyls include, for example, methyl, ethyl, n-propyl, isopropyl, n-butyl, t-butyl.

The term "alkylene" refers to both straight chained and branched chained alkylene groups and includes, for example,

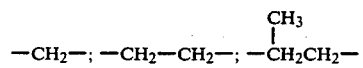

and the like.

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkylthio" refers to the group —SR' wherein R' is lower alkyl.

The term "lower alkoxyalkyl" refers to the group R'OR"— wherein R' and R" are independently straight chain or branched chain alkyl groups having 1 through 3 carbon atoms.

The term "lower alkylthioalkyl" refers to the group R'SR"— wherein R' and R" are independently straight chain or branched chain alkyl groups having 1 through 3 carbon atoms.

The term "lower alkoxycarbonylalkyl" refers to the group

wherein R' is lower alkyl and R" is alkylene having 1 through 4 carbon atoms and can be straight or branched chained. Typical alkoxycarbonylalkyl groups include for example, —CH$_2$C(O)OCH$_3$; —CH(CH$_3$)-C(O)OC$_2$H$_5$, and the like.

The term "halo" refers to the group of fluoro, chloro, bromo and iodo.

The term "lower haloalkyl" refers to haloalkyl compounds having 1 through 4 carbon atoms and 1 through 3 halo atoms independently selected from the group of fluoro, chloro, bromo and iodo. Preferably the lower haloalkyl group has 1 or 2 carbon atoms.

The term "lower haloalkoxy" refers to "lower alkoxy" groups having 1 through 3 halo atoms independently selected from the group of fluoro, chloro, bromo or iodo.

The term "aryl" refers to aryl groups having 6 through 10 carbon atoms and includes, for example, phenyl, naphthyl, indenyl. Typically the aryl group will be phenyl or naphthyl as compounds having such groups are more readily available commercially than other aryl compounds.

The term "substituted aryl" refers to aryl groups having 1 through 3 substituents independently selected from the group of lower alkyl, lower alkoxy, halonitro, or haloalkyl having 1 through 3 carbon atoms and 1 through 3 halo atoms. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "arylalkylene" refers to the group ArR$^3$— wherein Ar is aryl and R$^3$ is alkylene having 1 through 3 carbon atoms and includes both straight-chained and branched-chained alkylenes, for example, methylene, ethyl, 1-methylethyl, and propyl.

The term "(substituted aryl)alkylene" or "ring-substituted arylalkylene" refers to the group Ar'R$^3$— wherein Ar' is substituted aryl and R$^3$ is alkylene as defined with respect to arylalkylene.

The term "saturated nitrogen heterocycle" as used herein with respect to R$^1$ and R$^2$ of formula I refers to the groups having the formula:

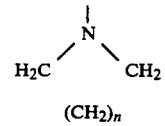

wherein n is 1, 2, or 3.

The term "compatible salts" refers to salts which do not significantly alter the herbicidal properties of the parent compound. Suitable salts include cation salts such as, for example, the cation salts of lithium, sodium, potassium, alkali earth metals, ammonia, quaternary ammonium salts, and the like.

The term "room temperature" or "ambient temperature" refers to about 20°–25° C.

Utility

The compounds of Formula (I) exhibit pre-emergence and post-emergence herbicidal activity. The compounds of Formula I wherein R is lower alkoxide exhibit superior herbicide activity and exhibit especially good pre-emergence herbicidal activity.

Generally, for post-emergent applications, the herbicidal compounds are applied directly to the foliage or other plant parts. For pre-emergence applications, the herbicidal compounds are applied to the growth medium, or prospective growth medium, for the plant. The optimum amount of the herbicidal compound or composition will vary with the particular plant species, and the extent of plant growth, if any, and the particular part of the plant which is contacted and the extent of contact. The optimum dosage can also vary with the general location, or environment (e.g., sheltered areas such as greenhouses compared to exposed areas such as fields), and type and degree of control desired. Generally, for both pre- and post-emergent control, the present compounds are applied at rates of about from 0.02 to 60 kg/ha, preferably about from 0.02 to 10 kg/ha.

Also, although in theory the compounds can be applied undiluted, in actual practice they are generally applied as a composition or formulation comprising an effective amount of the compound(s) and an acceptable carrier. An acceptable or compatible carrier (agriculturally acceptable carrier) is one which does not significantly adversely affect the desired biological effect achieved by the active compounds, save to dilute it. Typically, the composition contains about from 0.05 to 95% by weight of the compound of Formula (I) or mixtures thereof. Concentrates can also be made having high concentrations designed for dilution prior to application. The carrier can be a solid, liquid, or aerosol. The actual compositions can take the form of granules, powders, dusts, solutions, emulsions, slurries, aerosols, and the like.

Suitable solid carriers which can be used include, for example, natural clays (such as kaolin, attapulgite, montmorillonite, etc.), talcs, pyrophyllite, diatomaceous silica, synthetic fine silica, calcium aluminosilicate, tricalcium phosphate, and the like. Also, organic materials, such as, for example, walnut shell flour, cotton-seed hulls, wheat flour, wood flour, wood bark flour, and the like can also be used as carriers. Suitable liquid diluents which cam be used include, for example, water, organic solvents (e.g., hydrocarbons such as benzene, toluene, dimethylsulfoxide, kerosene, diesel fuel, fuel oil, petroleum naphtha, etc.), and the like. Suitable aerosol carriers which can be used include conventional aerosol carriers such as halogenated alkanes, etc.

The composition can also contain various promoters and surface-active agents which enhance the rate of transport of the active compound into the plant tissue such as, for example, organic solvents, wetting agents and oils, and in the case of compositions designed for pre-emergence application agents which reduce the leachability of the compound or otherwise enhance soil stability.

The composition can also contain various compatible adjuvants, stabilizers, conditioners, insecticides, fungicides, and if desired, other herbicidally active compounds.

At reduced dosages the compounds of the present invention also exhibit plant growth regulating activity and can be used to alter the normal growth pattern of green plants.

The compounds of Formula (I) can be applied as plant growth regulators in pure form, but more pragmatically, as in the case of herbicidal application, are applied in combination with a carrier. The same types of carriers as set forth hereinabove with respect to the herbicidal compositions can also be used. Depending on the desired application, the plant growth regulating composition can also contain, or be applied in combination with other compatible ingredients such as desiccants, defoliants, surface-active agents, adjuvants, fungicides, and insecticides. Typically, the plant growth regulating composition will contain a total of about from 0.005 to 90 wt. % of the compound(s) of Formula (I) depending on whether the composition is intended to be applied directly or diluted first.

A further understanding of the invention can be had in the following non-limiting Preparation and Examples. Wherein, unless expressly stated to the contrary, all temperatures and temperature ranges refer to the Centigrade system and the term "ambient" or "room temperature" refers to about 20°–25° C. The term "percent" or "%" refers to weight percent and the term "mole" or "moles" refers to gram moles. The term "equivalent" refers to a quantity of reagent equal in moles, to the moles of the preceding or succeeding reactant recited in that example in terms of finite moles or finite weight or volume. Where given, proton-magnetic resonance spectrum (p.m.r. or n.m.r.) were determined at 60 mHz, signals are assigned as singlets (s), broad singlets (bs), doublets (d), double doublets (dd), triplets (t), double triplets (dt), quartets (q), and multiplets (m); and cps refers to cycles per second. Also where necessary examples are repeated to provide additional starting material for subsequent examples.

EXAMPLES

EXAMPLE 1

(3-Trifluoromethylphenyl)-methoxyacetyl-acetonitrile

In this example, 4.7 g of sodium was added to 150 ml of anhydrous ethanol at room temperature resulting in the production of sodium ethanolate. The mixture was heated to reflux and 14 g of methyl methoxyacetate and 25 g of 3-trifluorololylacetate were slowly added to the refluxing mixture over a period of one hour. The mixture was refluxed for an additional 24 hours and then cooled and poured into 500 mls of water. The aqueous mixture was washed with petroleum ether, then acidified with aqueous 2M hydrochloric acid and extracted with methylene chloride. The methylene chloride extracts were combined, dried over magnesium sulfate and then evaporated affording 31.2 g of title compound as an oil residue.

Similarly, by adapting the above procedure using the appropriately substituted-phenyl acetonitrile and starting material, the following compounds can be prepared:
(5-chloro-3-trifluoromethylphenyl)-methoxyacetyl-acetonitrile;
(4-chloro-3-trifluoromethylphenyl)-methoxyacetyl-acetonitrile;
(2-bromo-3-trifluoromethylphenyl)-methoxyacetyl-acetonitrile;
(6-fluoro-3-trifluoromethylphenyl)-methoxyacetyl-acetonitrile;
(4-methyl-3-trifluoromethylphenyl)-methoxyacetyl-acetonitrile;
(5-methoxy-3-trifluoromethylphenyl)-methoxyacetyl-acetonitrile;
(6-methyl-3-trifluoromethylphenyl)-methoxyacetyl-acetonitrile;
(3,5-di-trifluoromethylphenyl)-methoxyacetyl-acetonitrile;
(3-difluoromethoxyphenyl)-methoxyacetyl-acetonitrile;
(3-trifluoromethoxyphenyl)-methoxyacetyl-acetonitrile;
(2-chloro-3-methylphenyl)-methoxyacetyl-acetonitrile;
(4-ethyl-3-methylphenyl)-methoxyacetyl-acetonitrile;
(5-methoxy-3-chlorophenyl)-methoxyacetyl-acetonitrile;
(3-iodophenyl)-methoxyacetyl-acetonitrile;
(3-difluoromethylthiophenyl)-methoxyacetyl-acetonitrile;
(3-trifluoromethylthiophenyl)-methoxyacetyl-acetonitrile;
(3,5-diethoxyphenyl)-methoxyacetyl-acetonitrile;

(3-bromophenyl)-methoxyacetyl-acetonitrile;
(2-chloro-3-methylphenyl)-methoxyacetyl-acetonitrile;
(3-chlorophenyl)-methoxyacetyl-acetonitrile;
(3-methylphenyl)-methoxyacetyl-acetonitrile;
(3-t-butoxyphenyl)-methoxyacetyl-acetonitrile;
(3-propylphenyl)-methoxyacetyl-acetonitrile;
(3-iodophenyl)-methoxyacetyl-acetonitrile; and
(3-methoxyphenyl)-1-methoxyacetyl-acetonitrile.

EXAMPLE 2

3-Oxo-4-(3-trifluoromethylphenyl)-5-amino-2,3-dihydrofuran

In this example a solution containing 31.7 g of (3-trifluoromethylphenyl)-methoxyacetyl-acetonitrile and 24.5 g of concentrated sulfuric acid in 125 ml of acetic acid was refluxed for about 15–20 minutes. The acetic acid was then evaporated off. The residue was mixed with ethyl ether and washed with saturated aqueous sodium bicarbonate solution. The mixture was then dried over magnesium sulfate. The ethyl ether was evaporated off and the residue triturated with a mixture of petroleum ether and ethyl ether affording 20.9 g of the title compound.

Similarly, by adapting the above procedure to the compounds listed in Example 1, the following compounds can be prepared:
3-oxo-4-(5-chloro-3-trifluoromethylphenyl)-5-amino-2,3-dihydrofuran;
3-oxo-4-(4-chloro-3-trifluoromethylphenyl)-5-amino-2,3-dihydrofuran;
3-oxo-4-(2-bromo-3-trifluoromethylphenyl)-5-amino-2,3-dihydrofuran;
3-oxo-4-(6-fluoro-3-trifluoromethylphenyl)-5-amino-2,3-dihydrofuran;
3-oxo-4-(4-methyl-3-trifluoromethylphenyl)-5-amino-2,3-dihydrofuran;
3-oxo-4-(5-methoxy-3-trifluoromethylphenyl)-5-amino-2,3-dihydrofuran;
3-oxo-4-(6-methyl-3-trifluoromethylphenyl)-5-amino-2,3-dihydrofuran;
3-oxo-4-(3,5-di-trifluoromethylphenyl)-5-amino-2,3-dihydrofuran;
3-oxo-4-(3-difluoromethoxyphenyl)-5-amino-2,3-dihydrofuran;
3-oxo-4-(3-trifluoromethoxyphenyl)-5-amino-2,3-dihydrofuran;
3-oxo-4-(2-chloro-3-methylphenyl)-5-amino-2,3-dihydrofuran;
3-oxo-4-(4-ethyl-3-methylphenyl)-5-amino-2,3-dihydrofuran;
3-oxo-4-(5-methoxy-3-chlorophenyl)-5-amino-2,3-dihydrofuran;
3-oxo-4-(3-iodophenyl)-5-amino-2,3-dihydrofuran;
3-oxo-4-(3-difluoromethylthiophenyl)-5-amino-2,3-dihydrofuran;
3-oxo-4-(3-trifluoromethylthiophenyl)-5-amino-2,3-dihydrofuran;
3-oxo-4-(3,5-diethoxyphenyl)-5-amino-2,3-dihydrofuran;
3-oxo-4-(3-bromophenyl)-5-amino-2,3-dihydrofuran;
3-oxo-4-(2-chloro-3-methylphenyl)-5-amino-2,3-dihydrofuran;
3-oxo-4-(3-chlorophenyl)-5-amino-2,3-dihydrofuran;
3-oxo-4-(3-methylphenyl)-5-amino-2,3-dihydrofuran;
3-oxo-4-(3-butoxyphenyl)-5-amino-2,3-dihydrofuran;
3-oxo-4-(3-propylphenyl)-5-amino-2,3-dihydrofuran; and
3-oxo-4-(3-iodophenyl)-5-amino-2,3-dihydrofuran;
3-oxo-4-(3-methoxyphenyl)-5-amino-2,3-dihydrofuran.

EXAMPLE 3

3-Oxo-4-(3-trifluoromethylphenyl)-5-dimethylamino-2,3-dihydrofuran

In this example, 36 g of 3-oxo-4-(3-trifluoromethylphenyl)-5-amino-2,3-dihydrofuran was suspended in 1 liter of methylene chloride at room temperture followed by the addition of 11.8 g of sodium hydrdoxide and 2.7 g of benzyl triethylammonium chloride dissolved in a small amount of water. A solution cntaining 37.3 g of dimethyl sulfate in 100 ml of methylene chloride was slowly added to the mixture at room temperature over a period of about two hours. The mixture was then stirred overnight (about 15–16 hours) at room temperature and then washed with water and dried over magnesium sulfate. The mixture was then evaporated affording 41.7 g of the title compound as the residue.

Similarly, by adapting the above procedure using the corresponding appropriately substituted starting materials, the following compounds can be prepared:
3-oxo-4-(5-chloro-3-trifluoromethylphenyl)-5-dimethylamino-2,3-dihydrofuran;
3-oxo-4-(4-chloro-3-trifluoromethylphenyl)-5-dimethylamino-2,3-dihydrofuran;
3-oxo-4-(2-bromo-3-trifluorometylphenyl)-5-dimethylamino-2,3-dihydrofuran;
3-oxo-4-(6-fluoro-3-trifluoromethylphenyl)-5-dimethylamino-2,3-dihydrofuran;
3-oxo-4-(4-methyl-3-trifluoromethylphenyl)-5-dimethylamino-2,3-dihydrofuran;
3-oxo-4-(5-methoxy-3-trifluoromethylphenyl)-5-dimethylamino-2,3-dihydrofuran;
3-oxo-4-(6-methyl-3-trifluoromethylphenyl)-5-dimethylamino-2,3-dihydrofuran;
3-oxo-4-(3,5-di-trifluoromethylphenyl)-5-dimethylamino-2,3-dihydrofuran;
3-oxo-4-(3-difluoromethylphenyl)-5-dimethylamino-2,3-dihydrofuran;
3-oxo-4-(3-trifluoromethoxyphenyl)-5-dimethylamino-2,3-dihydrofuran;
3-oxo-4-(2-chloro-3-methylphenyl)-5-dimethylamino-2,3-dihydrofuran;
3-oxo-4-(4-ethyl-3-methylphenyl)-5-dimethylamino-2,3-dihydrofuran;
3-oxo-4-(5-methoxy-3-chlorophenyl)-5-dimethylamino-2,3-dihydrofuran;
3-oxo-4-(3-iodophenyl)-5-dimethylamino-2,3-dihydrofuran;
3-oxo-4-(3-difluoromethylthiophenyl)-5-dimethylamino-2,3-dihydrofuran;
3-oxo-4-(3-trifluoromethylthiophenyl)-5-dimethylamino-2,3-dihydrofuran;
3-oxo-4-(3,5-diethoxyphenyl)-5-dimethylamino-2,3-dihydrofuran;
3-oxo-4-(3-bromophenyl)-5-dimethylamino-2,3-dihydrofuran;
3-oxo-4-(2-chloro-3-methylphenyl)-5-dimethylamino-2,3-dihydrofuran;
3-oxo-4-(3-chlorophenyl)-5-dimethylamino-2,3-dihydrofuran;
3-oxo-4-(3-methylphenyl)-5-dimethylamino-2,3-dihydrofuran;
3-oxo-4-(3-butoxyphenyl)-5-dimethylamino-2,3-dihydrofuran;

3-oxo-4-(3-propylphenyl)-5-dimethylamino-2,3-dihydrofuran; and
3-oxo-4-(3-iodophenyl)-5-dimethylamino-2,3-dihydrofuran;
3-oxo-4-(3-methoxyphenyl)-5-dimethylamino-2,3-dihydrofuran.

Similarly, by adapting the above procedure but using diethyl sulfate, the corresponding ethyl homologs of the above compounds can be prepared. By applying the procedures described on page 7, the corresponding 5-piperidin-1-yl and 5-(2-pyrrolin-1-yl) analogs can also be prepared.

EXAMPLE 4

2-Bromo-3-oxo-4-(3-trifluoro-methylphenyl)-5-dimethylamino-2,3-dihydrofuran

In the example, a mixture containing 0.7 g of 3-oxo-4-(3-trifluoromethylphenyl)-5-dimethylamino-2,3-dihydrofuran, 0.53 g of N-bromosuccinimide and 0.02 g of benzoyl peroxide in 25 ml of benzene was irradiated with 300–600 nm light for 2 hours. The mixture was then filtered and the filtrate evaporated to remove benzene. The residue was chromatographed eluting with 3% vol. tetrahyrofuran:97% methylene chloride. The product fractions were combined and evaporated affording 0.3 g of the title compound as the residue.

Similarly, by adapting the above procedure using the corresponding products from Example 3, the following compounds can be prepared:
2-bromo-3-oxo-4-(5-chloro-3-trifluoromethylphenyl)-5-dimethylamino-2,3-dihydrofuran;
2-bromo-3-oxo-4-(4-chloro-3-trifluoromethylphenyl)-5-dimethylamino-2,3-dihydrofuran;
2-bromo-3-oxo-4-(2-bromo-3-trifluoromethylphenyl)-5-dimethylamino-2,3-dihydrofuran;
2-bromo-3-oxo-4-(6-fluoro-3-trifluoromethylphenyl)-5-dimethylamino-2,3-dihydrofuran;
2-bromo-3-oxo-4-(4-methyl-3-trifluoromethylphenyl)-5-dimethylamino-2,3-dihydrofuran;
2-bromo-3-oxo-4-(5-methoxy-3-trifluoromethylphenyl)-5-dimethylamino-2,3-dihydrofuran;
2-bromo-3-oxo-4-(6-methyl-3-trifluoromethylphenyl)-5-dimethylamino-2,3-dihydrofuran;
2-bromo-3-oxo-4-(3,5-di-trifluoromethylphenyl)-5-dimethylamino-2,3-dihydrofuran;
2-bromo-3-oxo-4-(3-difluoromethoxyphenyl)-5-dimethylamino-2,3-dihydrofuran;
2-bromo-3-oxo-4-(3-trifluoromethoxyphenyl)-5-dimethylamino-2,3-dihydrofuran;
2-bromo-3-oxo-4-(2-chloro-3-methylphenyl)-5-dimethylamino-2,3-dihydrofuran;
2-bromo-3-oxo-4-(4-ethyl-3-methylphenyl)-5-dimethylamino-2,3-dihydrofuran;
2-bromo-3-oxo-4-(5-methoxy-3-chlorophenyl)-5-dimethylamino-2,3-dihydrofuran;
2-bromo-3-oxo-4-(3-iodophenyl)-5-dimethylamino-2,3-dihydrofuran;
2-bromo-3-oxo-4-(3-difluoromethylthiophenyl)-5-dimethylamino-2,3-dihydrofuran;
2-bromo-3-oxo-4-(3-trifluoromethylthiophenyl)-5-dimethylamino-2,3-dihydrofuran;
2-bromo-3-oxo-4-(3,5-diethoxyphenyl)-5-dimethylamino-2,3-dihydrofuran;
2-bromo-3-oxo-4-(3-bromophenyl)-5-dimethylamino-2,3-dihydrofuran;
2-bromo-3-oxo-4-(2-chloro-3-methylphenyl)-5-dimethylamino-2,3-dihydrofuran;
2-bromo-3-oxo-4-(3-chlorophenyl)-5-dimethylamino-2,3-dihydrofuran;
2-bromo-3-oxo-4-(3-methylphenyl)-5-dimethylamino-2,3-dihydrofuran;
2-bromo-3-oxo-4-(3-butoxyphenyl)-5-dimethylamino-2,3-dihydrofuran;
2-bromo-3-oxo-4-(3-propylphenyl)-5-dimethylamino-2,3-dihydrofuran; and
2-bromo-3-oxo-4-(3-iodophenyl)-5-dimethylamino-2,3-dihydrofuran;
2-bromo-3-oxo-4-(3-methoxyphenyl)-5-dimethylamino-2,3-dihydrofuran;
2-bromo-3-oxo-4-(3-trifluoromethylphenyl)-5-diethylamino-2,3-dihydrofuran;
2-bromo-3-oxo-4-(3-trifluoromethylphenyl)-5-(piperidin-1-yl)-2,3-dihydrofuran; and
2-bromo-3-oxo-4-(3-trifluoromethylphenyl)-5-(2-pyrrolin-1-yl)-2,3-dihydrofuran;

Similarly, by replacing N-bromosuccinimide with N-chlorosuccinimide or N-iodosuccinimide the corresponding 2-chloro and 2-iodo analogs of the above compounds can be prepared for example:
2-chloro-3-oxo-4-(3-trifluoromethylphenyl)-5-dimethylamino-2,3-dihydrofuran;
2-iodo-3-oxo-4-(3-trifluoromethylphenyl)-5-dimethylamino-2,3-dihydrofuran.

EXAMPLE 5

2-Ethoxy-3-oxo-4-(3-trifluoromethylphenyl)-5-dimethylamino-2,3-dihydrofuran

In this example, 0.16 g of sodium was added to 10 ml of anhydrous ethanol at room temperature resulting in the formation sodium ethoxide. A solution containing 2.5 g of 2-bromo-3-oxo-4-(3-trifluoromethylphenyl)-5-dimethylamino-2,3-dihydrofuran in 10 ml of ethanol was slowly added and the resulting mixture stirred at room temperature for one hour. The mixture was then evaporated to remove solvent. The residue was dissolved in methylene chloride, washed with water, dried over magnesium sulfate evaporated yielding in oil residue. The residue was chromatographed eluting with tetrahydrofuran:chloroform mixtures. The produced fractions afforded 1 g of the title compound.

Similarly, by adapting the same procedure using the corresponding dihydrofuran derivatives as starting materials, the following compounds can be prepared:
2-ethoxy-3-oxo-4-(5-chloro-3-trifluoromethylphenyl)-5-dimethylamino-2,3-dihydrofuran;
2-ethoxy-3-oxo-4-(4-chloro-3-trifluoromethylphenyl)-5-dimethylamino-2,3-dihydrofuran;
2-ethoxy-3-oxo-4-(2-bromo-3-trifluoromethylphenyl)-5-dimethylamino-2,3-dihydrofuran;
2-ethoxy-3-oxo-4-(6-fluoro-3-trifluoromethylphenyl)-5-dimethylamino-2,3-dihydrofuran;
2-ethoxy-3-oxo-4-(4-methyl-3-trifluoromethylphenyl)-5-dimethylamino-2,3-dihydrofuran;
2-ethoxy-3-oxo-4-(5-methoxy-3-trifluoromethylphenyl)-5-dimethylamino-2,3-dihydrofuran;
2-ethoxy-3-oxo-4-(6-methyl-3-trifluoromethylphenyl)-5-dimethylamino-2,3-dihydrofuran;
2-ethoxy-3-oxo-4-(3,5-di-trifluoromethylphenyl)-5-dimethylamino-2,3-dihydrofuran;
2-ethoxy-3-oxo-4-(3-difluoromethoxyphenyl)-5-dimethylamino-2,3-dihydrofuran;
2-ethoxy-3-oxo-4-(3-trifluoromethoxyphenyl)-5-dimethylamino-2,3-dihydrofuran;

2-ethoxy-3-oxo-4-(2-chloro-3-methylphenyl)-5-dimethylamino-2,3-dihydrofuran;
2-ethoxy-3-oxo-4-(4-ethyl-3-methylphenyl)-5-dimethylamino-2,3-dihydrofuran;
2-ethoxy-3-oxo-4-(5-methoxy-3-chlorophenyl)-5-dimethylamino-2,3-dihydrofuran;
2-ethoxy-3-oxo-4-(3-iodophenyl)-5-dimethylamino-2,3-dihydrofuran;
2-ethoxy-3-oxo-4-(3-difluoromethylthiophenyl)-5-dimethylamino-2,3-dihydrofuran;
2-ethoxy-3-oxo-4-(3-trifluoromethylthiophenyl)-5-dimethylamino-2,3-dihydrofuran;
2-ethoxy-3-oxo-4-(3,5-diethoxyphenyl)-5-dimethylamino-2,3-dihydrofuran;
2-ethoxy-3-oxo-4-(3-bromophenyl)-5-dimethylamino-2,3-dihydrofuran;
2-ethoxy-3-oxo-4-(2-chloro-3-methylphenyl)-5-dimethylamino-2,3-dihydrofuran;
2-ethoxy-3-oxo-4-(3-chlorophenyl)-5-dimethylamino-2,3-dihydrofuran;
2-ethoxy-3-oxo-4-(3-methylphenyl)-5-dimethylamino-2,3-dihydrofuran;
2-ethoxy-3-oxo-4-(3-butoxyphenyl)-5-dimethylamino-2,3-dihydrofuran;
2-ethoxy-3-oxo-4-(3-propylphenyl)-5-dimethylamino-2,3-dihydrofuran; and
2-ethoxy-3-oxo-4-(3-iodophenyl)-5-dimethylamino-2,3-dihydrofuran;
2-ethoxy-3-oxo-4-(3methoxyphenyl)-5-dimethylamino-2,3-dihydrofuran.

Similarly, by following the same procedure but using sodium methoxide, sodium isopropoxide, sodium butoxide, and sodium allyloxide in place of sodium ethoxide, the corresponding 2-methoxy, 2-isopropoxy 2-butoxy and 2-allyloxy analogs of the above compounds can be prepared, for example:
2-methoxy-3-oxo-4-(3-trifluoromethylphenyl)-5-dimethylamino-2,3-dihydrofuran;
2-isopropoxy-3-oxo-4-(3-trifluoromethylphenyl)-3-dimethylamino-2,3-dihydrofuran;
2-butoxy-3-oxo-4-(3-trifluoromethylphenyl)-5-dimethylamino-2,3-dihydrofuran; etc.

EXAMPLE 6

2-Fluoro-3-oxo-4-(3-trifluoromethylphenyl)-5-dimethylamino-2,3-dihydrofuran

In this example, a mixture containing 3 g of 2-bromo-3-oxo-4-(3-trifluoromethylphenyl)-5-dimethylamino-2,3-dihydrofuran, 0.26 of 18-Crown-6 ether and 1.11 g of potassium fluoride in 20 ml of acetonitrile was stirred at room temperature for about 30 minutes and then refluxed overnight (about 16 hours). The mixture was then cooled, filtered, and then concentrated by evaporation. The residue was chromatographed eluting with 3 vol. % tetrahydrofuran:97% chloroform affording the title compound.

EXAMPLE 7

Lithium salt of 2-ethoxy-3-oxo-4-(3-trifluoromethylphenyl)-5-methylamino-2,3-dihydrofuran ($R^1$=—$CH_3$, $R^2$=Li)

The above compound can be prepared by the following procedure.

In this example, 6.2 ml of 1.6M n-butyllithium in hexane is added dropwise to a stirred solution containing 2.86 g of 2-ethoxy-3-oxo-4-(3-trifluoromethylphenyl)-5-amino-2,3-dihydrofuran in 25 ml of tetrahydrofuran at −30° C. The resulting mixture is stirred for ½ to 2 hours, then concentrated in vacuo to afford the title compound.

EXAMPLE 8

The compounds listed in Table A hereinbelow were prepared using the appropriate starting materials and the appropriate procedures described in the Examples hereinabove.

TABLE A

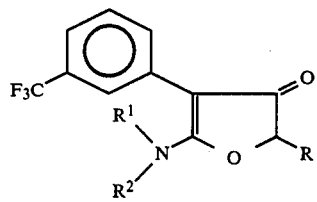

| No. | $R^1$ | $R^2$ | R | Carbon Calc. | Carbon Found | Hydrogen Calc. | Hydrogen Found | Nitrogen Calc. | Nitrogen Found | Melting Point °C. |
|---|---|---|---|---|---|---|---|---|---|---|
| 1 | $CH_3$ | $CH_3$ | Br | 44.57 | 47.16 | 3.14 | 4.26 | 4 | 4.27 | oil |
| 2 | $CH_3$ | $CH_3$ | —$OC_2H_5$ | 57.14 | 53.65 | 5.08 | 4.77 | 4.44 | 2.32 | semi-solid |
| 3 | $CH_3$ | $CH_3$ | —$O(CH_2)_2CH_3$ | 58.36 | 56.05 | 5.47 | 5.77 | 4.26 | 4.49 | 82–83 |
| 4 | $CH_3$ | $CH_3$ | —O—$CH(CH_3)_2$ | 58.36 | 55.49 | 5.47 | 5.47 | 4.26 | 4.79 | oil |
| 5 | $CH_3$ | $CH_3$ | —O—$CH_2CH=CH_2$ | 58.72 | 56.08 | 4.89 | 5.34 | 4.28 | 4.35 | 56–59 |
| 6 | $CH_3$ | $CH_3$ | —$OCH_3$ | 55.81 | 55.89 | 4.65 | 4.77 | 4.65 | 5.17 | 116–120 |

TABLE C
COMPARISON COMPOUNDS

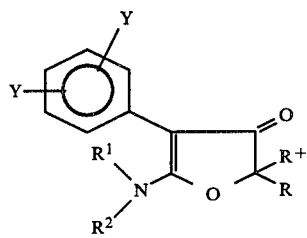

(unless otherwise noted X = H and R+ = H)

| No. | $R^1$ | $R^2$ | R | Y | ELEMENTAL ANALYSIS | | | | | | Melting Point °C. |
|---|---|---|---|---|---|---|---|---|---|---|---|
| | | | | | Carbon | | Hydrogen | | Nitrogen | | |
| | | | | | Calc. | Found | Calc. | Found | Calc. | Found | |
| C-1 | $CH_3$ | $CH_3$ | φ | H | 77.42 | 75.64 | 6.09 | 6.39 | 5.02 | 5.03 | 111–115 |
| C-2 | H | H | H | H | 68.57 | 68.99 | 5.14 | 5.78 | 8.0 | 7.87 | 221–223* |
| C-3 | H | H | H | 3-Cl | 57.29 | 51.6 | 6.68 | 5.67 | 3.82 | 3.7 | 214–216* |
| C-4 | H | H | H | 4-Cl | 57.29 | 53.46 | 6.68 | 5.52 | 3.82 | 4.11 | 169–170* |
| C-5 | $CH_3$ | H | H | 4-Cl | 59.07 | 59.34 | 4.48 | 5.03 | 6.27 | 6.02 | 133–137* |
| C-6 | $CH_3$ | $CH_3$ | H | 4-Cl | 60.64 | 58.61 | 5.05 | 5.24 | 5.90 | 5.76 | 161–163 |
| C-7 | $CH_3$ | H | φ | 4-Cl | 68.1 | 64.4 | 4.7 | 5.3 | 4.7 | 4.5 | oil |
| C-8 | H | H | H | 4-$CH_3$ | 69.84 | 67.98 | 5.82 | 5.63 | 7.41 | 6.7 | 189–191* |
| C-9 | $CH_3$ | H | H | 4-$CH_3$ | 70.94 | 70.85 | 6.4 | 6.63 | 6.9 | 6.96 | 151–156* |
| C-10 | H | H | φ | 4-$CH_3$ | 77.0 | 76.2 | 5.7 | 5.9 | 5.3 | 5.05 | 142–146 |
| C-11 | $CH_3$ | H | φ | 4-$CH_3$ | 77.4 | 75.49 | 6.1 | 6.14 | 5.0 | 4.89 | 148–154 |
| C-12 | H | H | φ | 4-$OCH_3$ | 72.6 | 70.5 | 5.4 | 6.0 | 5.0 | 4.8 | 138–141 |
| C-13 | $CH_3$ | $CH_3$ | φ | 4-$OCH_3$ | 73.8 | 72.9 | 6.2 | 6.7 | 4.5 | 4.7 | 140–143 |
| C-14 | ** | H | φ | 3-$CF_3$ | 62.7 | 62.4 | 3.4 | 4.5 | 6.35 | 5.8 | oil |
| C-15 | $CH_3$ | $CH_3$ | R = φ, R+ = Cl | 3-$CF_3$ | 59.76 | 57.9 | 3.93 | 4.06 | 3.67 | 3.56 | oil |
| C-16[2] | H | H | φ | Y = 3-Cl, X = 4-Cl | 60.0 | 60.1 | 3.5 | 3.7 | 4.4 | 4.8 | 179–182 |

C-16[2] is 2-phenyl-3-oxo-4-(3,4-dichlorophenyl)-5-amino-2,3-dihydrofuran
*Decomposition
**4-$NO_2$φ—

EXAMPLE 9

In this example, the compounds of Tables A and C were respectively tested using the procedures described hereinbelow for pre-emergent and post-emergent activity against a variety of grasses and broad-leaf plants including one grain crop and one broad-leaf crop. The compounds tested are identified by compound number in Tables A and C hereinabove.

Pre-Emergent Herbicide Test

Pre-emergence herbicidal activity was determined in the following manner.

Test solutions of the respective compounds were prepared as follows:

355.5 mg of test compound was dissolved in 15 ml of acetone. 2 ml of acetone containing 110 mg of a nonionic surfactant was added to the solution. 12 ml of this stock solution was then added to 47.7 ml of water which contained the same nonionic surfactant at a concentration of 625 mg/l.

Seeds of the test vegetation were planted in a pot of soil and the test solution was sprayed uniformly onto the soil surface either at a dose of 27.5 micrograms/cm² or in some instances as indicated in Table 1 hereinbelow, certain of the compounds were tested at a lower dosage of 15.6 micrograms/cm². The pot was watered and placed in a greenhouse. The pot was watered intermittently and observed for seedling emergence, health of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests are summarized in Table 1.

Post-Emergent Herbicidal Test

The test compound was formulated in the same manner as described above for the pre-emergent test. This formulation was uniformly sprayed on 2 similar pots containing plants 2 to 3 inches tall (except wild oats, soybean and watergrass which were 3 to 4 inches tall) (approximately 15 to 25 plants per pot) at a dose of 27.5 microgram/cm². After the plants had dried, they were placed in a greenhouse and then watered intermittently at their bases as needed. The plants were observed periodically for phytotoxic effects and physiological and morphological responses to the treatment. After 3 weeks, the herbicidal effectiveness of the compound was rated based on these observations. A 0-to-100 scale was used, 0 representing no phytotoxicity, 100 representing complete kill. The results of these tests are summarized in Table 2.

TABLE 1
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs quarter | Mustard | Pigweed | Soybean | Crabgrass | Watergrass | Wild Oats | Rice |
| 1 | 0 | 0 | 0 | 0 | 0 | 0 | 0 | 0 |
| 2 | 100 | 100 | 100 | 97 | 100 | 100 | 100 | 93 |
| 3 | 100 | 100 | 100 | 99 | 100 | 100 | 100 | 97 |
| 4 | 100 | 100 | 100 | 100 | 100 | 100 | 100 | 97 |
| 5 | 97 | 100 | 100 | 80 | 97 | 89 | 30 | 15 |

TABLE 1-continued

Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs quarter | Mustard | Pigweed | Soybean | Crabgrass | Watergrass | Wild Oats | Rice |
| 6 | 80 | 60 | 95 | 75 | 88 | 85 | 0 | 0 |

TABLE 1A

COMPARISON COMPOUNDS
Pre-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs quarter | Mustard | Pigweed | Soybean | Crabgrass | Watergrass | Wild Oats | Rice |
| C-1 | 40 | 25 | 40 | 0 | 75 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 30 | 25 | 0 | 40 | 0 | 0 | 0 | 0 |
| C-9 | 0 | 0 | 0 | 0 | 0 | 0 | 0 | 0 |
| C-10 | 0 | 0 | 0 | 0 | 0 | 0 | 0 | 0 |
| C-11 | 0 | 0 | 0 | 0 | 30 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 45 | 35 | 0 | 0 |
| C-15 | 0 | 0 | 0 | 0 | 0 | 0 | 0 | 0 |
| C-16 | 0 | 0 | 0 | 0 | 0 | 0 | 0 | 0 |

TABLE 2

Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs quarter | Mustard | Pigweed | Soybean | Crabgrass | Watergrass | Wild Oats | Rice |
| 1 | 30 | 15 | 0 | 15 | 0 | 0 | 0 | 0 |
| 2 | 70 | 80 | 80 | 60 | 0 | 0 | 0 | 0 |
| 3 | 65 | 99 | 60 | 75 | 0 | 0 | 0 | 0 |
| 4 | 45 | 70 | 50 | 40 | 0 | 0 | 0 | 0 |
| 5 | 40 | 80 | 40 | 35 | 0 | 0 | 0 | 0 |
| 6 | 40 | 40 | 45 | 35 | 0 | 0 | 0 | 0 |

TABLE 2A

COMPARISON COMPOUNDS
Post-Emergence Herbicidal Activity
Application Rate: 27.5 micrograms/cm², unless otherwise noted

| Compound No. | Broad-Leaf Plants % Phytotoxicity | | | | Grasses % Phytotoxicity | | | |
|---|---|---|---|---|---|---|---|---|
| | Lambs quarter | Mustard | Pigweed | Soybean | Crabgrass | Watergrass | Wild Oats | Rice |
| C-1 | 20 | 20 | 0 | 25 | 0 | 0 | 0 | 0 |
| C-2 | 0 | 0 | 0 | 0 | 0 | 0 | 0 | 0 |
| C-3 | 0 | 0 | 0 | 0 | 0 | 0 | 0 | 0 |
| C-4 | 0 | 0 | 0 | 0 | 0 | 0 | 0 | 0 |
| C-5 | 0 | 0 | 0 | 0 | 0 | 0 | 0 | 0 |
| C-6 | 0 | 0 | 0 | 0 | 0 | 0 | 0 | 0 |
| C-7 | 0 | 0 | 0 | 0 | 0 | 0 | 0 | 0 |
| C-8 | 25 | 20 | 25 | 30 | 0 | 0 | 0 | 0 |
| C-9 | 20 | 20 | 10 | 25 | 0 | 0 | 0 | 0 |
| C-10 | 0 | 0 | 0 | 0 | 0 | 0 | 0 | 0 |
| C-11 | 20 | 0 | 0 | 20 | 0 | 0 | 0 | 0 |
| C-12 | 0 | 0 | 0 | 0 | 0 | 0 | 0 | 0 |
| C-13 | 0 | 0 | 0 | 0 | 0 | 0 | 0 | 0 |
| C-14 | 0 | 0 | 0 | 0 | 0 | 0 | 0 | 0 |
| C-15 | 25 | 25 | 0 | 30 | 25 | 10 | 45 | 45 |
| C-16 | 0 | 0 | 0 | 0 | 0 | 0 | 0 | 0 |

Obviously, many modifications and variations of the invention described hereinabove and below can be made without departing from the essence and scope thereof.

What is claimed is:

1. A compound having the formula:

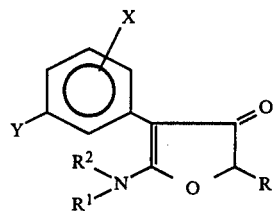

(I)

wherein

R is fluoro, chloro, bromo, iodo, lower alkoxy having 1 through 6 carbon atoms or alkenylmethoxy having 3 through 8 carbon atoms;

$R^1$ is alkyl having 1 through 4 carbon atoms;

$R^2$ is alkyl having 1 through 4 carbon atoms, alkenyl having 3 or 4 carbon atoms, lower alkoxycarbonylalkyl, lower alkoxyalkyl or lower alkylthioalkyl; or $R^1$ and $R^2$ together with the nitrogen atom to which they are joined form a saturated nitrogen heterocycle having 4- through 6-ring atoms one of which is the joining nitrogen and the remainder are carbon atoms or an unsaturated heterocycle selected from the group of 2-pyrrolin-1-yl; 3-pyrrolin-1-yl; 1,2,3,4-tetrahydropyrid-1-yl or 1,2,5,6-tetrahydropyrid-1-yl;

X is hydrogen, lower alkyl, lower alkoxy, halo, or trifluoromethyl and can be at any available position on the phenyl ring; and Y is lower alkyl, lower alkoxy, halo, lower haloalkyl having 1 through 4 carbon atoms and 1 through 3 of the same or different halo atoms, lower haloalkoxy having 1 through 4 carbon atoms and 1 through 3 of the same or different halo atoms, or lower haloalkylthio having 1 through 4 carbon atoms and 1 through 3 of the same or different halo atoms;

and compatible salts thereof.

2. The compound of claim 1 wherein one of $R^1$ or $R^2$ is methyl, ethyl or propyl.

3. The compound of claim 1 wherein $R^1$ and $R^2$ are each independently methyl or ethyl.

4. The compound of claim 1 wherein $R^1$ and $R^2$ are are each methyl.

5. The compound of claim 1 wherein X is hydrogen.

6. The compound of claim 2 wherein X is hydrogen.

7. The compound of claim 3 wherein X is hydrogen.

8. The compound of claim 1 wherein R is chloro, bromo or iodo.

9. The compound of claim 8 wherein R is bromo.

10. The compound of claim 1 wherein R is fluoro.

11. The compound of claim 1 wherein R is lower alkoxy or alkenylmethoxy.

12. The compound of claim 11 wherein X is hydrogen and $R^1$ and $R^2$ are independently selected from the group of hydrogen, methyl or ethyl.

13. The compound of claim 1 wherein R is ethoxy, propoxy, isopropoxy or t-butoxy.

14. The compound of claim 13 wherein R is ethoxy, propoxy or isopropoxy.

15. The compound of claim 13 wherein $R^1$ and $R^2$ are independently, methyl or ethyl.

16. The compound of claim 15 wherein R is ethoxy, propoxy or isopropoxy.

17. The compound of claim 16 wherein $R^1$ and $R^2$ are each methyl.

18. The compound of claim 17 wherein X is hydrogen.

19. A compound having the formula:

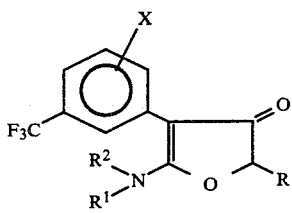
(I)

wherein
R is fluoro, chloro, bromo, iodo, lower alkoxy, or alkenylmethoxy having 3 through 8 carbon atoms;
$R^1$ is alkyl having 1 through 4 carbon atoms;
$R^2$ is alkyl having 1 through 4 carbon atoms, alkenyl having 3 or 4 carbon atoms, lower alkoxycarbonylalkyl, lower alkoxyalkyl or lower alkylthioalkyl; or
$R^1$ and $R^2$ together with the nitrogen atom to which they are joined form a saturated nitrogen heterocycle having 4- through 6-ring atoms one of which is the joining nitrogen atom and the remainder of which are carbon atoms or an unsaturated heterocycle selected from the group of 2-pyrrolin-1-yl; 3-pyrrolin-1-yl; 1,2,3,4-tetrahydropyrid-1-yl; or 1,2,5,6-tetrahydropyrid-1-yl;
X is hydrogen, lower alkyl, lower alkoxy, halo, or trifluoromethyl and can be at any available position on the phenyl ring;
and compatible salts thereof.

20. The compound of claim 19 wherein $R^1$ and $R^2$ are independently methyl or ethyl.

21. The compound of claim 19 wherein $R^1$ and $R^2$ are each methyl.

22. The compound of claim 19 wherein X is hydrogen and R is chloro, bromo, or iodo.

23. The compound of claim 22 wherein $R^1$ and $R^2$ are each methyl.

24. The compound of claim 19 wherein R is bromo.

25. The compound of claim 19 wherein R is fluoro.

26. The compound of claim 19 wherein R is lower alkoxy or alkenylmethoxy having 3 through 6 carbon atoms.

27. The compound of claim 19 wherein R is ethoxy, propoxy, isopropoxy, t-butoxy, or allyloxy.

28. The compound of claim 19 wherein R is ethoxy, propoxy or isopropoxy.

29. The compound of claim 28 wherein $R^1$ and $R^2$ are independently methyl or ethyl.

30. The compound of claim 29 wherein $R^1$ and $R^2$ are each methyl.

31. The compound of claim 29 wherein X is hydrogen.

32. The compound of claim 19 wherein X is hydrogen.

33. The compound of claim 1 wherein Y is a lower haloalkyl having 1 or 2 carbon atoms.

34. A herbicidal composition comprising a herbicidally effective amount of a compound according to claim 11, or mixtures of such compounds, and a compatible carrier.

35. A herbicidal composition comprising a herbicidally effective amount of a compound according to claim 31, or mixtures thereof, and a compatible carrier.

36. A method for controlling plants which comprises applying a herbicidally effective amount of a compound according to claim 1, or mixtures thereof, to the foliage or potential growth medium of said plants.

37. A method for preventing or destroying plants which comprises applying a herbicidally effective amount of a compound according to claim 31, or mixtures thereof, to the foliage or potential growth medium of said plants.

38. A method for regulating the growth of plants which comprises applying to the foliage of said plants or their growth medium an amount of a compound according to claim 1, or mixtures thereof, effective to alter the growth pattern of such plants.

39. A process for preparing the compound of claim 1 wherein R is lower alkoxy or alkenylmethoxy which comprises the steps of:
(a) contacting the corresponding compound having the formula:

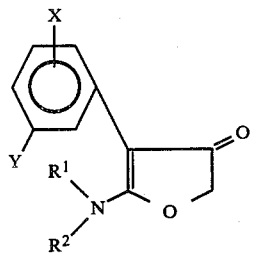
(A)

wherein $R^1$, $R^2$, X and Y are as defined in claim 1; with a halosuccinimide selected from the group consisting of N-bromosuccinimide, N-chlorosuccinimide and N-iodosuccinimide under ultra-violet irradiation thereby yielding the corresponding compound having the formula:

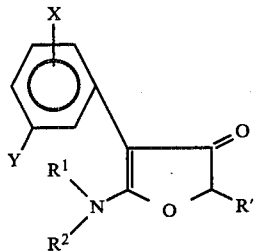

wherein $R^1$, $R^2$, X and Y are as defined hereinabove and R' is chloro, bromo, or iodo; and
(b) contacting the product of step (a) with an alkali metal lower alkoxide or alkenylmethoxide under reactive conditions, thereby yielding the corresponding compound of claim 1 wherein R is lower alkoxy or alkenylmethoxy.

40. The process of claim 39 wherein said step (a) is conducted in the presence of a halogenation catalyst.

* * * * *